United States Patent [19]

Bender et al.

[11] 4,398,031

[45] Aug. 9, 1983

[54] COUMARIN DERIVATIVES AND METHOD FOR SYNTHESIZING 5'-METHYL PSORALENS THEREFROM

[75] Inventors: Dean R. Bender, Hazlet, N.J.; John E. Hearst; Henry Rapoport, both of Berkeley, Calif.

[73] Assignee: The Regents of the University of California, Berkeley, Calif.

[21] Appl. No.: 356,271

[22] Filed: Mar. 9, 1982

Related U.S. Application Data

[63] Continuation of Ser. No. 158,599, Jun. 11, 1980, abandoned.

[51] Int. Cl.$^3$ ............................................ C07D 405/02
[52] U.S. Cl. ...................................... 549/282; 549/289
[58] Field of Search ............................................ 549/282

[56] References Cited

U.S. PATENT DOCUMENTS 3,201,421 8/1965 Kaufman ............................ 549/282
4,124,598 11/1978 Hearst et al. ......................... 424/180

OTHER PUBLICATIONS

J. Org. Chem., 44, (1979), 2176–2180, Bender et al.
J. Org. Chem., 39, (1974), 2656–2657, Trehan et al.
J. Am. Chem. Soc., 89, (1967), 4457–4458, Nienhouse et al.
J. Org. Chem., 26, (1961), 117–121, Kaufman.
J.C.S. Perkin I, 1, (1976), Anderson et al.
Tetrahedron Lett, No. 10, (1967), 859–861, Kaminsky et al.
J. Heterocycl. Chem., 3, (1966), 42–45, Noel et al.
Gazz. Chim. Stal., 88, (1958), 415–428, Antonello.
Aust J. Chem., 25, (1972), 1537–1542, Pordanani et al.
J. Org. Chem., 27, (1962), 2931–2933, Kaiser et al.
J. Am. Chem. Soc., 58, (1936), 2190–2193, Hurd et al.
Biochemistry, 16, (1977), 1053–1064, Isaacs et al.

Primary Examiner—Jane T. Fan
Attorney, Agent, or Firm—Majestic, Gallagher, Parsons & Siebert

[57] ABSTRACT

Two species of a coumarin derivative are disclosed, both of which may be produced from a 7-hydroxycoumarin precursor. The one species is an oxime and the other is a β-haloallyl ester.

A method for making a psoralen compound in high yield comprises treating these coumarin derivatives with an acid to fuse a furan ring thereto, and recovering a 5'-methyl psoralen therefrom. The 5'-methyl psoralen may be produced in up to about 70% overall yield with respect to the 7-hydroxycoumarin precursor.

10 Claims, No Drawings

COUMARIN DERIVATIVES AND METHOD FOR SYNTHESIZING 5'-METHYL PSORALENS THEREFROM

This is a continuation, of Ser. No. 158,599, filed June 11, 1980 now abandoned.

BACKGROUND OF THE INVENTION

1. Field of the Invention

This invention relates to psoralen compounds, and more particularly to 5'-methyl psoralens synthesized from coumarin derivatives having a common hydroxycoumarin precursor.

2. Prior Art

Psoralens are the linear isomers of the furocoumarin family and they occur naturally in certain fruits and seeds, e.g., *Ammi majus* and *Psoralea corylifolia*. Extracts of these fruits and seeds have been used since ancient times as dermal sensitizing agents in the treatment of vitiligo. Topical application of psoralen extracts, followed by irradiation with light, results in a stimulation of melanin production, thus producing a dermal "tanning" effect.

In recent years, psoralens have been utilized in the photo-chemotherapy of psoriasis. In such treatment, psoralens are administered orally or topically to a patient. Subsequently, the skin is exposed to ultra-violet radiation. A high percentage of remissions of the disease occur after such treatment.

With increasing study of, and interest in, molecular biology, the psoralens have been investigated with respect to their ability to form covalent bonds with nucleic acids. Because of their planar structure, psoralens can intercalate between the base pairs in the double helix molecular structure of nucleic acids. Upon irradiation with light of the proper wavelength, the psoralens may form covalent bonds with pyrimidine nucleotides that occur as integral entities of nucleic acid strands. Achieving covalently bonded psoralen bridges or cross-links between the nucleic acid strands of the double helix presents another tool for use in studying, in vivo, secondary structures of nucleic acids. In addition, the psoralens provide a means for inactivating viruses for the purpose of vaccine production, and also as potential chemotherapeutic agents. The covalently bonded psoralens act as inhibitors of DNA replication and thus have the potential to slow down, or stop, the replication process. The covalent bond can only be produced in a two step process by first intercalating the psoralen into the nucleic acid helix, and second by exposing those sites to electromagnetic radiation. Thus, it is immediately apparent that the covalent bonding can be controlled both temporally and spacially.

4,5',8-trimethylpsoralen and its derivatives have drawn particular attention as effective photoreactive cross-linking reagents for nucleic acids. These 5'-methylpsoralens may be synthesized from the readily available hydroxy-coumarins. However, the prior known synthesizers have proceeded only moderately or poorly, and the yields of 5'-methylpsoralen therefrom have been relatively low. For example, one approach has been reported by K. D. Kaufman, *J. Org. Chem.*, Vol. 26, 117 (1961), which utilizes Claisen rearrangement of 7-allyoxycoumarins. The last step thereof requires use of alkali and gives an overall yield from hydroxycoumarin of 28%.

Accordingly, a good and general method for synthesizing 5'-methylpsoralens in high yield has been hiterto lacking.

SUMMARY OF THE INVENTION

The present invention is concerned with a coumarin derivative having two species and a method for synthesizing 5'-methylpsoralens in high yield.

In one aspect of the present invention, a method for making a 5'-methylpsoralen compound comprises the steps of providing a coumarin derivative selected either from an oxime species or a haloallyl ester species thereof. The coumarin derivative is then treated with an acid or mixture of acids at a predetermined temperature. Such treatment fuses a furano ring moiety to the coumarin derivative. A resultant product, produced in high yield, is 5'-methylpsoralen.

The oxime species and the haloallyl ester species of the coumarin derivative are both provided from a 7-hydroxycoumarin precursor. The inventive method yields 5'-methylpsoralens of from about 40% to about 70% overall with respect to the 7-hydroxycoumarin.

Other aspects and advantages of the invention will become apparent from the following description and appended claims.

DETAILED DESCRIPTION OF THE PREFERRED EMBODIMENTS

The basic psoralen structure (and ring numbering therefor) is

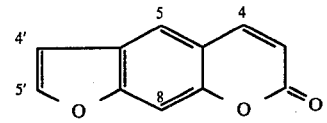

while the two most widely known and widely used derivatives are 8-methoxy psoralen (commonly called -methoxsalen):

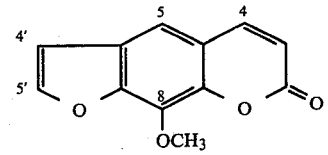

and 4,5',8-trimethyl psoralen (commonly called -trioxsalen):

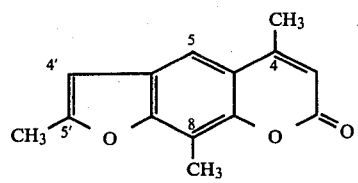

The 5'-methylpsoralen trioxsalen is particularly useful as a pigmentation agent (a photosensitizer), and a number of useful psoralens may be further synthesized therefrom. For example, 4'-adducts of trioxsalen are disclosed by U.S. Pat. No. 4,124,598, issued Nov. 7, 1978, inventors John E. Hearst, et al., which adducts are conveniently synthesized from trioxsalen.

Psoralens are members of the furocoumarin family as they include a furano moiety fused to a coumarin moiety. The basic coumarin structure is

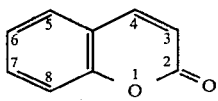

while the basic furan structure is

7-hydroxycoumarins are readily commercially available and have the basic structure

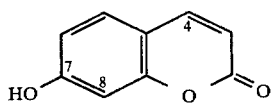

A variety of organic radicals are known as substituents at the 4 and 8 locations. The new coumarin derivatives are derived from these precursor 7-hydroxycoumarins, are useful for making 5'-methylpsoralens, and are of two species.

One species, sometimes hereinafter referred to as the oxime species or as derivative (2), is a 7-coumaryl oxime having the structure

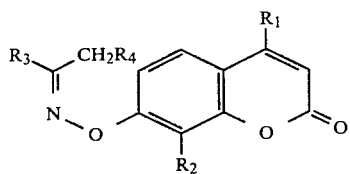

wherein $R_1$ and $R_2$ may be a variety of organic radicals known to the art, for example, alkyl, aryl and alkyl-aryl; $R_1$ and $R_2$ may also be hydrogen, and $R_2$ may be an alkoxy, and, $R_3$ and $R_4$ are various alkyls and may also be hydrogen.

The other species, sometimes hereinafter referred to as to the β-haloallyl species or as derivative (1), is a haloallyl ester coumarin derivative having the structure

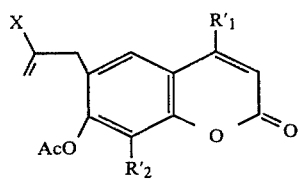

wherein $R_1'$ and $R_2'$ are as previously described for $R_1$ and $R_2$ of the oxime species; In addition, $R_2'$ can be formyl or acyl, for example, acetyl; and, X is a halogen.

Specific examples of the new coumarin derivatives are 7-acetoxy-6-(β-chloroallyl)-4,8-dimethylcourmarin (of the β-haloallyl species):

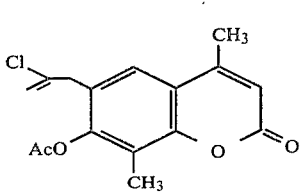

And, acetone 0-7-(4,8-dimethylcoumaryl)oxime (of the oxime species):

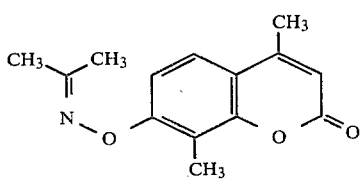

The oxime and the β-haloallyl species of the coumarin derivatives are useful as intermediates in the production of 5'-methylpsoralens. Their use to produce 5'-methyl psoralens shall hereinafter be more specifically described. Both species are novel compounds in their own right; the synthesis of the β-haloallyl species (Examples I-III), and then of the oxime species (Examples IV-VI) shall now be described.

Synthesis Of The Coumarin Derivatives

For convenience, all syntheses are presented as specific examples, but it should be understood that larger or smaller quantities may be produced in accordance with the methods set forth. Also, variations in the methods set forth will become apparent to those skilled in the art. All temperatures hereinafter reported are in centigrade, $T_b$ is bath temperature and $T_i$ is internal temperature.

EXAMPLE I

Crude 7-β-Chloroallyloxy)-4,8-dimethylcoumarin 4,8-dimethyl-7-hydroxycoumarin (19.0 g, 0.10 mol) and DMF (143 ml, dried over 4 A sieves) were heated at 70° ($T_b$) with mechanical stirring until the 4,8-dimethyl-7-hydroxycoumarin dissolved; then benzene (143 ml), $K_2CO_3$ (18.7 g, 0.13 mol), KI (0.86 g, 5 mmol) and 2,3-dichloro-1-propene (13.1 g, 0.118 mol, bp 92°-93°) were added in the order given. The mixture was mechanically stirred at 80°-85° ($T_b$) for 11 h, cooled, and evaporated at 15 mm to remove benzene, then at 0.1 mm to remove DMF. The residue was diluted with $CHCl_3$ (400 ml) and washed with water (55 ml). The aqueous layer was extracted further with $CHCl_3$ (100 ml), and the combined extracts were washed with 1 M NaOH (400 ml), then with saturated NaCl (400 ml), and dried. Evaporation gave 26.3 g (99%) of solid, giving on TLC ($CH_2Cl_2$) one spot corresponding in $R_f$ with 7-(β-chloroallyloxy)-4,8-dimethylcoumarin, which was purified as described in Example II, below.

EXAMPLE II

Purified 7-(β-Chloroallyloxy)-4,8-dimethylcoumarin 1.33 g (7 mmol) of 4,8-dimethyl-7-hydroxycoumarin was converted to the product as described by Example I and then purified for analysis as follows.

Chromatography on silica gel (15 g) with $CHCl_3$ yielded a residue (1.82 g, 98%) which was recrystallized from CHCl3/hexanes to give after collection of three crops 1.67 g (90%) of 7-β-chloroallyloxy)-4,8-dimethylcoumarin: mp 117°–118°; NMR δ 2.37 (3H, s), 2.38 (3H, d, J=2 Hz), 4.68 (2H, m), 5.55 (2H, m, $J_{gem}$=7 Hz), 6.14 (1H, m), 6.82 (1H, d, J=9 Hz), 7.44 (1H, d, J=9 Hz); UV (95% $C_2H_5OH)\lambda_{max}$ 244 nm (ε 3920), 254 (4120), 319 (14,600).

Anal. Calcd for $C_{14}H_{13}O_3Cl$: C, 63.5; H, 5.0. Found: C, 63.7; H, 5.1.

EXAMPLE III

7-Acetoxy-6-(β-chloroallyl)-4,8-dimethylcoumarin

A portion of the purified 7-(β-chloroallyloxy)-4,8-dimethylcoumarin of Example II, (264 mg, 1.0 mmol) was added to p-diisopropylbenzene (4 ml, refluxed over Na for 16 hr, then distilled from Na) and acetic anhydride (0.4 ml). This mixture was refluxed ($T_i$ 195°) under argon for 26 h. The cooled reaction mixture was diluted with CHCl3 (5 ml), washed with water (10 ml) and then with NaHCO3 (10 ml), dried and evaporated at 15 mm to remove CHCl3, then at 0.1 mm/50° to remove p-diisopropylbenzene. The residue was chromatographed on silica gel (2.8 g) eluting with $CH_2Cl_2$ to yield a residue (300 mg) which was recrystallized from CHCl3/hexanes to give 7-acetoxy-6-(β-chloroallyl)-4,8-dimethylcoumarin (185 mg, 60%): mp 161°–162°; NMR δ 2.27 (3H, s) 2.38 (3H, s), 2.42 (3H, d, J=2 Hz), 3.64 (2H, broad s), 5.25 (2H, m, $J_{gem}$=11 Hz), 6.28 (1H, m), 7.40 (1H, broad s); UV (95% $C_2H_5OH)\lambda_{max}$ 244 nm (sh, ε 7090), 278 (11,800), 315 (6900).

Analysis Calculated for $C_{16}H_{15}O_4Cl$: C, 62.7; H, 4.9. Found: C, 62.6; H, 5.0.

EXAMPLE IV

7-Aminoxy-4,8-dimethylcoumarin

Sodium hydride (220 mg, 50% NaH in oil dispersion) was diluted and stirred with dry hexane (6 ml). The mixture was allowed to settle and the hexane was drawn off. This process was repeated twice, then the residue was dried by sweeping $N_2$ through the flask while stirring. To the residue (142 mg, 5.9 mmol NaH) was added DMF (13 ml, distilled from $CaH_2$) and the mixture was cooled in an ice-water bath. 4,8-dimethyl-7-hydroxycoumarin (1.12 g, 5.9 mmol) in DMF (11 ml) was added dropwise over 5 min while maintaining $T_i$ at 5°–10° to form the anionic form of the hydroxycoumarin. The cooling bath was removed after 0.5 h, and 0-(2,4-dinitrophenyl)hydroxylamine (588 mg, 2.95 mmol) in DMF (7 ml) was added over 3 min. The solution was stirred for 3 h and then added with stirring and cooling to a solution of water (175 ml) and saturated NaHCO3 (42 ml) followed by extraction with CHCl3 (1×175 ml plus 2×75 ml). The combined extracts were cooled to 5°–10° and washed with cold 1 M NaOH (175 ml) and then with saturated NaHCO3 (100 ml), dried and evaporated to a residue (0.42 g, 69%). This material was compared by TLC and spectral studies with verified 7-aminoxy-4,8-dimethylcoumarin from Example V below, and found to be identical therewith.

EXAMPLE V

Verification of 7-aminoxy-4,8-dimethylcoumarin 64 mg of material was prepared as described by Example IV, and was recrystallized from absolute ethanol to yield 50 mg of fine needles: mp 155°–156° (dec); NMR (DMSO-$d_6$) δ 2.20 (3H, s), 2.42 (3H, d, J=2 Hz), 6.18 (1H, m), 7.22 (2H, br s), 7.44 (1H, d, J=9 Hz), 7.62 (1H, d, J=9 Hz); UV (95% $C_2H_5OH)\lambda_{max}$ 247 nm (ε 3720), 256 (3690), 324 (16,200).

Analysis Calculated for $C_{11}H_{11}NO_3$: C, 64.4; H, 5.4; N, 6.8. Found: C, 64.1; H, 5.4; N, 7.1.

EXAMPLE VI

Acetone 0-7-(4,8-dimethylcoumaryl)oxime 205 mg (1.0 mmol) of the 7-aminoxy-4,8-dimethylcoumarin of Example IV was combined with absolute ethanol (10 ml), acetone (64 mg, 0.081 ml, 1.1 mmol) and conc. HCl (2 drops) in the order given and stirred. Within 5 min this heterogeneous mixture had become homogeneous, and within another 10 min it was heterogeneous. After 1 h the mixture was evaporated to a residue (237 mg) which was chromatographed on silica gel (2 g) with $CH_2Cl_2$ to yield a residue which on recrystallization from absolute ethanol yielded 211 mg (86%) of acetone 0-7-(4,8-dimethylcoumaryl)oxime: mp 129°–130° (dec.); NMR δ 2.08 (3H, s), 2.15 (3H, s) 2.3 (3H, s), 2.40 (3H, d, J=2 Hz), 6.08 (1H, m), 7.38 (2H, s); UV (95% $C_2H_5OH)\lambda_{max}$ 248 nm (ε 5880), 257 (5830), 323 (18,400).

Analysis Calculated for $C_{14}H_{15}NO_3$: C, 68.6; H, 6.2; N, 5.7. Found: C, 68.5; H, 6.2; N, 5.7.

Thus, Examples I-III may be summarized by the following general reaction schematic, Scheme A (wherein $R_1'$, $R_2'$ and X are as have been previously described, and "derivative (1)" represents the β-haloallyl species in accordance with the present invention).

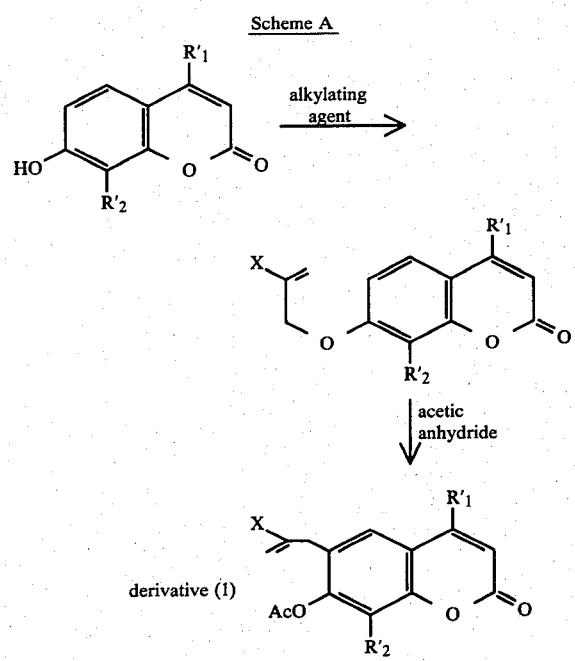

Scheme A

The intermediate compound of Scheme A, above, is normally a β-haloallyl ether which does not require extensive purification for conversion to derivative (1), although chromatography is recommended. Where the intermediate compound is to be a chloroallyl ether, the preferred alkylating agent is 2,3-dichloro-1-propene. When $R_2'$ is formyl or acetyl the acetic anhydride may be omitted in the rearrangement step and thus the product (i.e., derivative (1)) will be phenol rather than its acetate.

Examples IV-VI may be summarized by the following general reaction scheme, Scheme B (wherein $R_1$, $R_2$, $R_3$ and $R_4$ are as have been previously described, and "derivative (2)" represents the oxime species in accordance with the present invention).

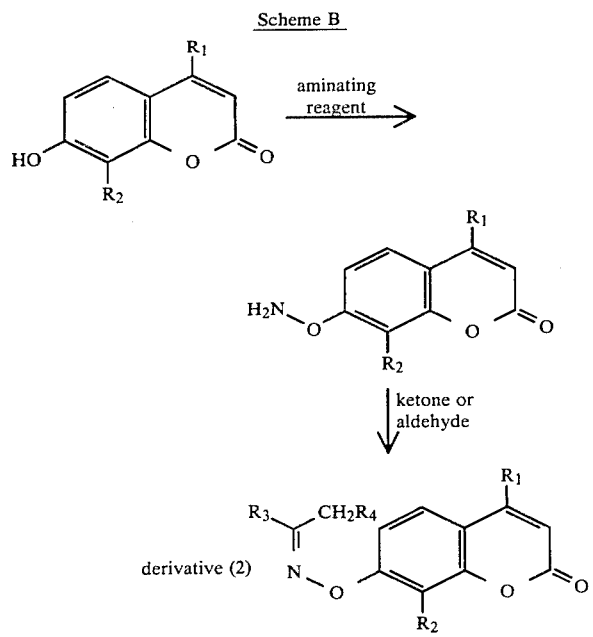

Scheme B

A large number of ketones or aldehydes are suitable for use in reaction Scheme B, and $R_3$, $R_4$ will derive from the particular ketone or aldehyde utilized. For example, when acetone is utilized, $R_4 = H$ and $R_3 = CH_3$. Conversion of the phenol, or 7-hydroxycoumarin in Scheme B with the aminating reagent (preferably 0-(2,4-dinitrophenyl)hydroxylamine) may be by a 1:1 mole ratio; however, better yield can be obtained with an excess of 7-hydroxycoumarin, preferably wherein the 7-hydroxycoumarin is a 2:1 mole ratio with respect to aminating reagent.

METHOD FOR MAKING PSORALENS

Broadly, a method for making a 5'-methyl psoralen in accordance with the present invention comprises treating derivative (1) or derivative (2), as represented above, with sufficient of an acid or mixture of acids at a predetermined temperature range to fuse a furano ring moiety thereto. When derivative (1) is provided, the treating is with sulfuric acid of a concentration not greater than about 85%, more preferably from about 70% to about 80%, most preferably at about 70%, the treating being at a temperature of from about 0° C. to about 25° C., to form a 5'-methyl psoralen. The 5'-methyl psoralen reaction product from such treatment is recoverable in high, overall yield with respect to the hydroxycoumarin precursor, which precursor is common to both derivatives (1) and (2). The inventive method shall now be more particularly described for derivatives (1) and (2) respectively.

Examples VI-IX illustrate the method, or aspects thereof, when derivative (1) is provided. Similarly, Examples X-XII illustrate the method, or aspects thereof, when derivative (2) is provided.

EXAMPLE VI

Treatment of derivative (1), wherein $R_1' = -CH_3$, $R_2' = -CH_3$ and $X = -Cl$, with concentrated $H_2SO_4$ at room temperature (about 18° to about 25°) led to rapid consumption of derivative (1), but no product could be isolated.

EXAMPLE VII

Treatment of derivative (1), wherein $R_1' = CH_3$, $R_2' = -CH_3$ and $X = -Cl$, with 90% $H_2SO_4$ at from about 0°-5° allowed for isolation of two products as follows.

To 90% (v/v) sulfuric acid (4 ml) at 0°-5° ($T_i$) was added with magnetic stirring derivative (1) [100 mg, 0.32 mmol] over 1.5 min. After 10 min the solution was added dropwise over 1 min to 30 ml water with rapid stirring and cooling. The mixture was extracted with $CHCl_3$ (2×10 ml), and the combined extracts were dried and evaporated to yield a residue (56 mg) which was chromatographed on kieselgel (6 g) with $CHCl_3$ to yield 4,5',8-trimethylpsoralen (18 mg) and a dimer (29 mg): NMR δ 1.87 (3H, s), 2.32 (3H, d, J=2 Hz), 2.38 (3H, s), 2.42 (3H, d, J=2 Hz), 2.52 (3H, s), 2.58 (3H, s), 3.60 (2H, m), 6.02 (1H, m), 6.15 (1H, m), 7.22 (1H, s), 7.55 (1H, s); MS m/e (rel. intensity) 457 (11%), 456 (37, M+), 228 (39), 44 (100); high resolution mass spectrum, calcd for $C_{28}H_{24}O_6$ (M+), 456.1573, found, 456.1558.

If the above reaction in 90% sulfuric acid was allowed to continue for more than 1.5 h, both products were no longer present.

EXAMPLE VIII

Derivative (1), where $R_1' = -CH_3$, $R_2' = -CH_3$ and $X = -Cl$, was treated with 80% $H_2SO_4$ at about 0°-5° in a manner analogous to Example VII. Again, two products were isolated (that is, the desired 5'-methylpsoralen and a dimer thereof), but the relative amount of dimer was decreased.

EXAMPLE IX

Derivative (1), where $R_1' = -CH_3$, $R_2' = -CH_3$ and $X = -Cl$, [7.47 g, 24.4 mmol] was shaken on a mechanical shaker with 70% (v/v) sulfuric acid (171 ml conc. $H_2SO_4$ plus 74 ml water) for 1.0 h. The mixture was then added to water (1.72 L) with vigorous mechanical stirring at a rate which allowed maintenance of $T_i$ at 10°-20°. The mixture was then extracted with chloroform (2×500 ml). The combined extracts were washed with saturated $NaHCO_3$ (600 ml), cooled to 5° and washed with cold 1 M NaOH (400 ml), and then washed with saturated $NaHCO_3$ (400 ml), dried and evaporated to a residue which was recrystallized from $CHCl_3$/ethyl acetate to yield 4,5',8-trimethylpsoralen (4.48 g, 80%): mp 231°-232° (lit. reports a mp 234°-235°; mp of material purchased from the Paul B. Elder Company, 230°-231°); identical by TLC, NMR and UV comparison with authentic material; NMR δ 2.52 (6H, m), 2.57 (3H, s), 6.20 (1H, m), 6.40 (1H, m), 7.50 (1H, broad s).

EXAMPLE X

Derivative (2), where $R_1 = -CH_3$, $R_2 = -CH_3$, $R_3 = -CH_3$ and $R_4 = -H$, [245 mg, 1.0 mmol] was dissolved in 88% formic acid (30 ml), then 85% $H_3PO_4$ (3.3 ml) was added and the solution was stirred at 60° ($T_b$) for 4 h. The cooled reaction solution was added to cold water (200 ml) with stirring and cooling, and this solution was extracted with $CHCl_3$ (2×125 ml). The combined extracts were washed with saturated NaHCO₃ (100 ml), with 1 M NaOH (100 ml), then again with saturated NaHCO₃ (75 ml), dried and evaporated to a residue (188 mg, 82%) which was chromatographed on kieselgel (20 g) with CH₂Cl₂ to separate 4,5',8-trimethylpsoralen (94 mg, 41%).

EXAMPLE XI

Derivative (2), where $R_1$, $R_2$ and $R_3$ =—CH₃, and $R_4$=—H, was treated as in Example X, above, but acetic acid was utilized rather than the formic acid. An overall yield of about 40%, 4,5,8-trimethylpsoralen was obtained.

EXAMPLE XII

Derivative (2) was treated as in Example X, above, but formic acid alone (i.e. without phosphoric acid) was utilized which adequately converted the oxime species to trimethylpsoralen.

In summary, the present invention provides a good, general method for synthesizing 5'-methylpsoralens in high yield.

We claim:

1. A method for making a psoralen compound comprising the steps of:

prioviding a coumarin derivative of the structure

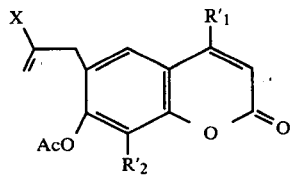

wherein $R_1'$ is —H or —CH₃, $R_2'$ is —CH₃, —OCH₃,

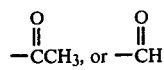

and X is a halogen;
treating said coumarin derivative with sulfuric acid, a concentration of said sulfuric acid being from about 70% to about 80%, the treating being at a temperature of from about 0° to about 25° C.; and
recovering a product compound from the treating step, said product compound being a 5'-methyl psoralen having the structure

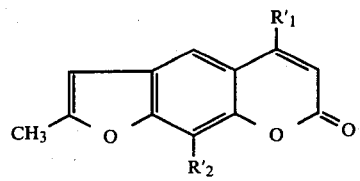

2. A method for making a psoralen compound comprising the steps of:

alkylating a quantity of 7-hydroxy-coumarin with an alkylating agent, said alkylating agent having a halogen, to form a β-haloallyl ether coumarin;
heating said β-haloallyl ether coumarin in the presence of an acetic anhydride to produce a coumarin derivative of the structure

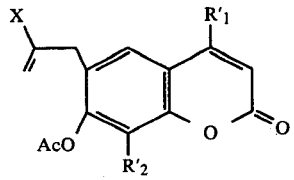

wherein $R_1'$ is —H or —CH₃, $R_2'$ is —CH₃, —OCH₃, $$-\overset{O}{\underset{\parallel}{C}}CH_3, \text{ or } -\overset{O}{\underset{\parallel}{C}}H$$

and X is a halogen;
treating said coumarin derivative with sulfuric acid, a concentration of said sulfuric acid being not greater than about 85%, the treating being at a temperature of from about 0° C. to about 25° C., to form a 5'-methyl psoralen of the structure 3. The method as in claim 2 wherein X is —Cl.

4. The method as in claim 2 wherein the concentration of said sulfuric acid is from about 70% to about 80%.

5. The method as in claim 2 wherein the concentration of said sulfuric acid is about 70% and the treating is at a temperature of from about 18° C. to about 25° C.

6. The method as in claim 2 wherein $R_1'$ and $R_2'$ of said coumarin derivative and of said product compound are —CH₃.

7. The method as in claim 2 wherein said β-haloallyl ether coumarin is a β-chloroallyl ether coumarin, and said alkylating agent is 2,3-dichloro-1-propene.

8. The method as in claim 7 further comprising:
isolating said β-chloroallyl ether coumarin formed from said alkylating step by chromatography prior to the heating step, and isolating said coumarin derivative produced by said heating step by chromatography prior to said treating step.

9. The method as in claim 2 further comprising the step of:
recovering said 5'-methyl psoralen as a product compound from the treating step.

10. The method as in claim 1 wherein:
the concentration of said sulfuric acid is about 70% and the recovering of said product compound is in high yield.

* * * * *

UNITED STATES PATENT AND TRADEMARK OFFICE
CERTIFICATE OF CORRECTION

PATENT NO. : 4,398,031

DATED : Aug. 9, 1983

INVENTOR(S) : Bender et al.

It is certified that error appears in the above-identified patent and that said Letters Patent is hereby corrected as shown below:

Col. 6, line 60: "either" should be --ether--.

Col. 9, line 28: "prioviding" should be --providing--.

Signed and Sealed this

Twenty-seventh Day of December 1983

[SEAL]

Attest:

GERALD J. MOSSINGHOFF

Attesting Officer     Commissioner of Patents and Trademarks